United States Patent
Penenberg et al.

[11] Patent Number: 5,989,259
[45] Date of Patent: Nov. 23, 1999

[54] FEMORAL CALCAR STOP FOR USE WITH FEMORAL STEM INSERTER

[75] Inventors: Brad Penenberg, Los Angeles, Calif.; Anthony P. Sanders, Lakeville; Patricia Katzman, Arlington., both of Mass.

[73] Assignee: Johnson & Johnson Professional, Inc., Raynham, Mass.

[21] Appl. No.: 09/139,635

[22] Filed: Aug. 25, 1998

[51] Int. Cl.⁶ .................................................. A61B 17/58
[52] U.S. Cl. ............................................ 606/99; 606/102
[58] Field of Search ............................... 606/85, 99, 100, 606/102

[56] References Cited

U.S. PATENT DOCUMENTS

| | | | |
|---|---|---|---|
| 4,642,121 | 2/1987 | Keller | 623/18 |
| 4,790,852 | 12/1988 | Noiles | 623/18 |
| 5,514,136 | 5/1996 | Richelsoph | 606/99 |
| 5,540,697 | 7/1996 | Rehmannn et al. | 606/91 |
| 5,584,837 | 12/1996 | Petersen | 606/91 |
| 5,683,469 | 11/1997 | Johnson et al. | 623/20 |

*Primary Examiner*—Michael Buiz
*Assistant Examiner*—Julian W. Woo
*Attorney, Agent, or Firm*—Nutter, McClennen & Fish, LLP

[57] ABSTRACT

A prosthetic stem inserter device includes an elongate rod member having a handle portion and an elongate rod member having a distal portion which has a plurality of surface features formed thereon which define a series of predetermined stem insertion depths. The device further includes a depth guide member having a proximal portion removably and replaceably engageable with the surface features on the elongate rod member. A distal, bone engaging portion of the depth guide member protrudes beyond a distal end of the elongate rod member. The depth guide member includes a mounting plate having a substantially hemispherical opening slot therein and a pair of distally extending prong elements. Each prong element has a first, longitudinally extending portion and a second portion that is angled with respect to the first portion. The second portion is adapted for contacting a plane of calcar bone in a prepared femoral cavity when a femoral stem is inserted into the cavity.

13 Claims, 4 Drawing Sheets

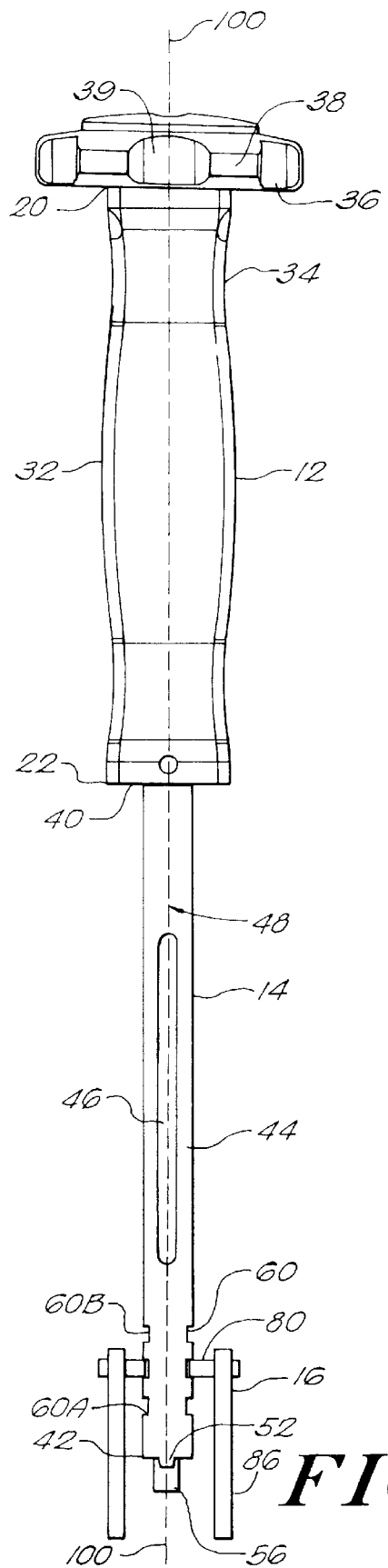
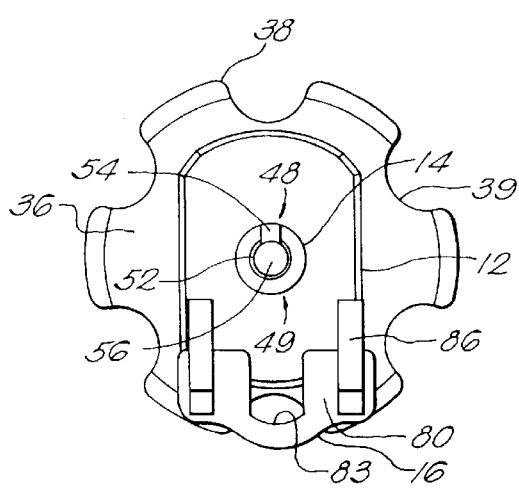
FIG. 2
FIG. 3

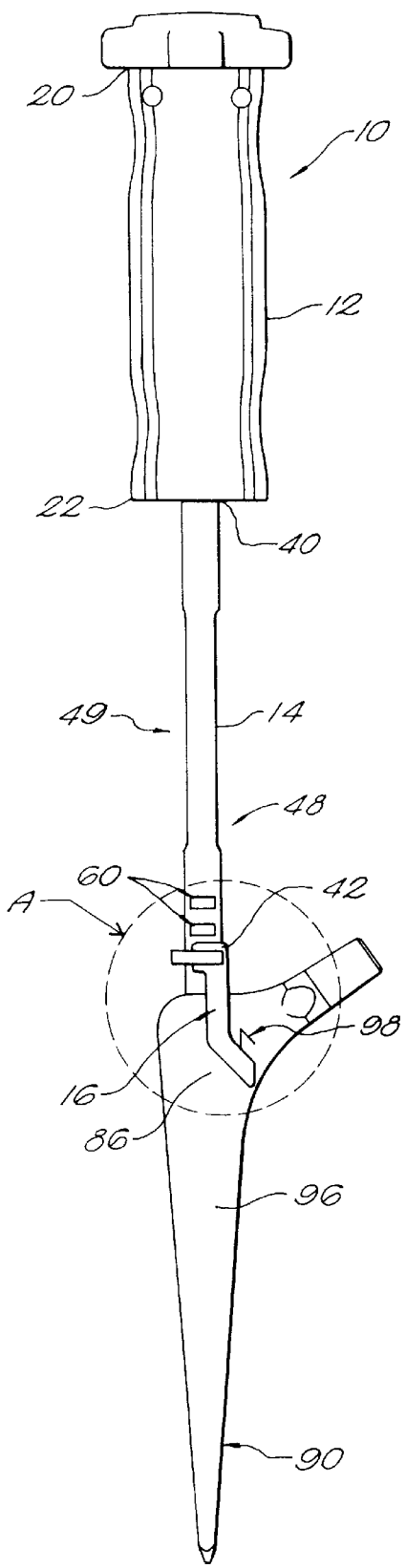
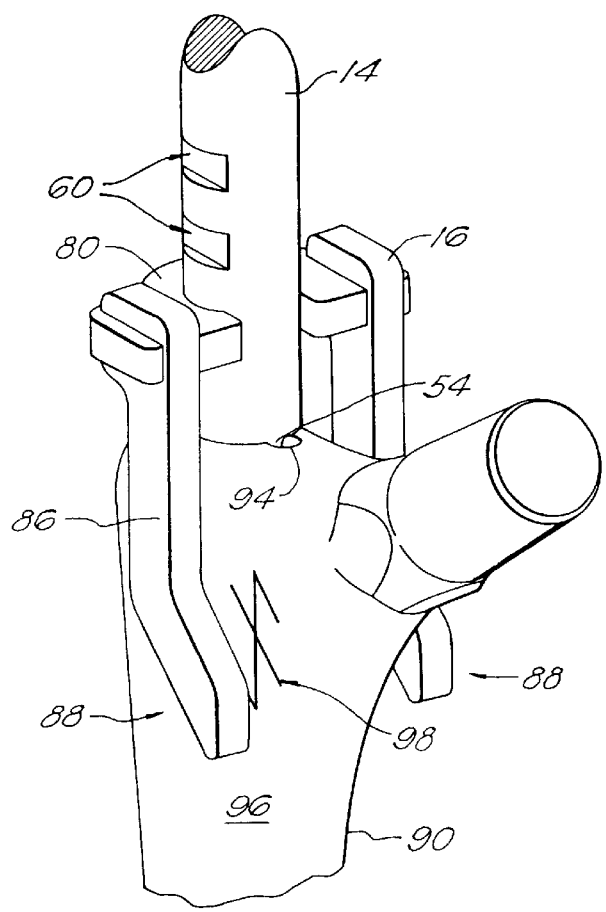
FIG. 6
FIG. 7

5,989,259

FEMORAL CALCAR STOP FOR USE WITH FEMORAL STEM INSERTER

CROSS-REFERENCE TO RELATED APPLICATIONS

Not Applicable.

STATEMENT REGARDING FEDERALLY SPONSORED RESEARCH

Not Applicable.

FIELD OF THE INVENTION

The present invention relates to joint prostheses, and more particularly to a device for inserting a prosthesis component within a bone cavity.

BACKGROUND OF THE INVENTION

Joint replacement surgery is quite common and enables many individuals to function normally when otherwise it would not be possible to do so. One of the more common prosthetic joint implants is the artificial hip joint. The artificial hip joint is made up of several components, including a femoral component and an acetabular component or shell. The femoral component includes an elongate stem or shaft which is mounted within the medullary canal of the femur.

In the course of hip replacement surgery, a cavity for receiving the prosthesis stem is reamed in the bone. The stem can be designed to be cemented within the cavity, to be press-fit within the cavity, or to rely on both cemented and press-fit fixation. The stem must be properly positioned and oriented within the cavity to enable proper functioning of the hip joint.

With some cemented stems, it can be difficult to determine the proper depth of the stem within the cavity. Some stems include a proximal collar that mounts upon the proximal end of the prepared femur to provide proper depth positioning. However, collarless stems can be more difficult to seat at the proper depth. If improperly implanted, the stem must be then removed and reinserted, increasing operative time.

Accordingly, it would be desirable to provide a device which facilitates the insertion of a prosthetic stem of an orthopedic implant into a prepared bone cavity at a desired depth.

SUMMARY OF THE INVENTION

A prosthetic stem inserter device is provided which includes a handle portion and an elongate rod member having a proximal end and a distal end which has a plurality of surface features formed thereon which define a series of predetermined stem insertion depths. The device further includes a depth guide member having a proximal portion removably and replaceably engageable with the surface features on the elongate rod member. A distal, bone engaging portion of the depth guide member is also provided which protrudes beyond a distal end of the elongate rod member when the depth guide member is engaged with the surface features on the elongate rod member.

In one embodiment, the depth guide member includes a mounting plate and a pair of distally extending prong elements. The mounting plate has a substantially hemispherical slot or recess formed therein with a thickness sufficient to enable the plate member to be engaged with the surface features of the elongate rod member such that the plate extends in a direction substantially transverse to the longitudinal axis of the elongate rod member. Each prong element has a first, longitudinally extending portion and a second portion that is angled with respect to the first portion. The second portion is adapted for contacting a plane of calcar bone in a prepared femoral cavity when a femoral stem is inserted into the cavity.

BRIEF DESCRIPTION OF THE DRAWINGS

The invention will be more fully understood by reference to the following detailed description when considered in conjunction with the accompanying drawings, in which:

FIG. 2 is a top view of the stem inserter device of FIG. 1.

FIG. 3 is an end view of the stem inserter device of FIG. 1.

FIG. 6 is a side view of the stem inserter device of FIG. 1 when attached to a femoral stem implant.

FIG. 7 is a detailed perspective view of portion A shown in FIG. 6.

DETAILED DESCRIPTION OF THE INVENTION

Figure 1:
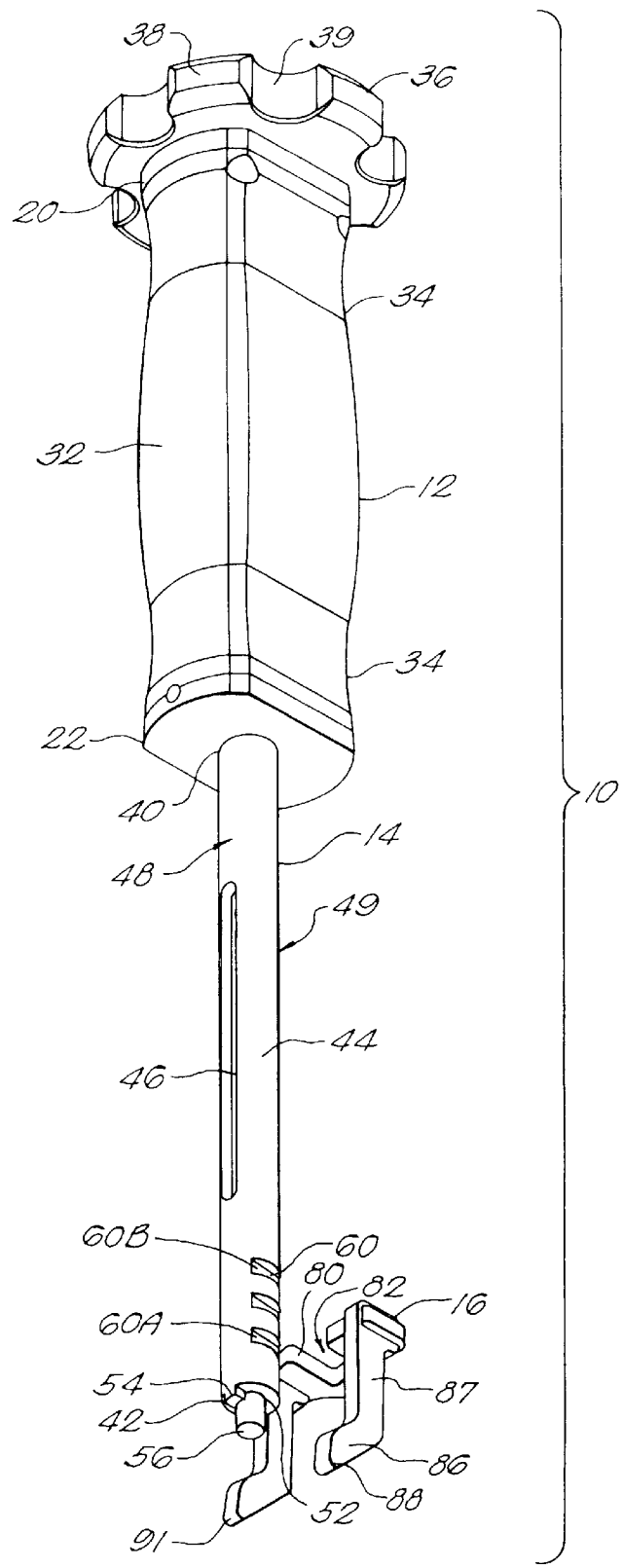
FIG. 1 is an unassembled perspective view of a prosthetic stem inserter device according to the present invention.
Figure 4A:
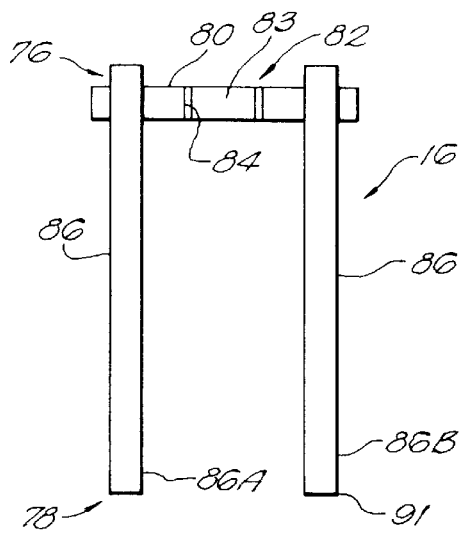
FIG. 4A is a top view of a depth guide member for use with the stem inserter device of FIG. 1.
Figure 4B:
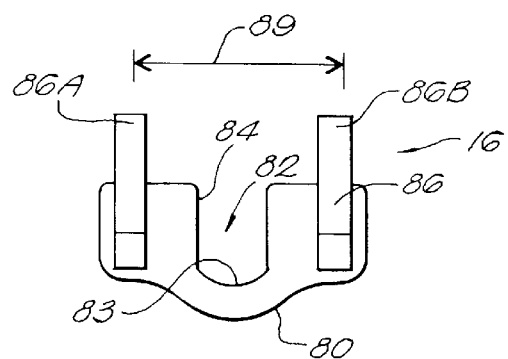
FIG. 4B is a end view of the depth guide member of FIG. 4A.
Figure 4C:
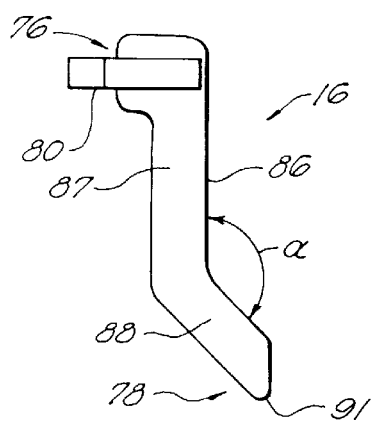
FIG. 4C is a side view of the depth guide member of FIG. 4A.

Referring to FIGS. 1–3, a modular stem inserter device 10 of the present invention is shown. The stem inserter device 10 includes a handle portion 12, an elongate rod member 14, and a depth guide member 16. In an exemplary embodiment, the depth guide member 16 is removably and replaceably disposed on a distal end 42 of the elongate rod member 14. The stem inserter device 10 as shown is used to insert a prosthetic component, such as a femoral hip stem, at a desired depth within a prepared femoral bone cavity.

As illustrated in FIGS. 1–3, the exemplary handle 12 is elongate and has opposed proximal and distal ends 20, 22. The shape and dimensions of the handle 12 may be selected by a person of ordinary skill in the art to allow the handle 12 to be suitably grasped by a surgeon in an operating environment. In an exemplary embodiment, the handle 12 may include surface contours such as raised areas 32 and indentations 34 which conform to the human hand. The handle 12 may also include a proximal end cap 36 which has alternating surface features 38, 39 formed thereon to further aid in deployment of the stem inserter device 10.

A generally cylindrical elongate rod member 14 extends distally from the handle portion 12. The elongate rod member 14 has proximal and distal ends 40, 42 with an outer surface 44 extending therebetween with first or top sides 48 and second or bottom sides 48, 49. Preferably, the proximal end 40 of elongate rod member 14 extends a suitable distance into the distal end 22 of handle 12 to properly secure the rod member 14 to the handle 12. In an exemplary embodiment, the elongate rod member 14 may have a longitudinally extending slot 46 formed therein and extending between the top and bottom sides 48, 49 to allow for the flushing through of cleansing fluids after an operative stem insertion procedure.

The outer surface 44 proximate the distal end 42 of elongate stem member 14 also has formed thereon a set positioning elements or surface features 60 which, in one embodiment, can be in the form of grooves or indentations. The surface features 60 are generally parallel to each other and extend in a direction generally transverse to a longitudinal axis 100 of the elongate rod member 14. In an exemplary embodiment, the surface features 60 are uniformly spaced apart in the longitudinal direction by a distance in the range of 2 to 8 mm. The surface features are dimensioned to securely engage depth guide member 16 and may have a depth in the range of about 2 to 4 mm and a height in the range of about 2 to 5 mm. Although the surface features 60 are illustrated as grooves, one of ordinary skill in the art will appreciate that other structures, such as protrusions, may alternatively be used.

The surface features 60 allow the positioning of the depth guide member 16 in a range of positions along the elongate rod member 14 which correspond to predetermined stem insertion depths. For example, if it is desirable to insert a femoral stem 90, as illustrated in FIGS. 6 and 7, at a relatively shallow depth, the depth guide member 16 can be positioned and mounted within the distal-most groove 60A. Similarly, if it is desirable to mount the stem at a relatively deeper insertion depth, the depth guide member 16 can be mounted within the proximal-most groove 60B. Although the stem inserter device 10 of the drawings includes three pairs of opposed grooves, those of ordinary skill in the art will recognize that any number of grooves can be formed in the outer surface 44 of elongate rod member 14.

The distal end 42 of elongate rod member 14 further includes a distally facing surface 52. In an exemplary embodiment, at least one anti-rotation tab member 54 extends distally from surface 52 at the top side 48 of elongate rod member 14. The anti-rotation tab member 54 has a size and shape effective to engage a notch 94, shown in FIG. 7, that is typically formed in the femoral stem 90 to prevent the stem inserter device 10 from rotating while attached to the femoral stem 90.

In an exemplary embodiment, the distally facing surface 52 further includes a stem securing member 56. The generally cylindrical stem securing member 56 extends distally from surface 52 and preferably, has a diameter less than a diameter of the elongate rod member 14. The stem securing portion 56 may have threads formed thereon effective to threadably engage a corresponding threaded portion, not shown, formed within a cavity in a proximal portion of the femoral stem 90. In such a threaded engagement, the stem securing portion 56 secures the stem inserter device 10 to the femoral stem implant.

Referring to FIGS. 1, 2 and 4A–4C, the depth guide member 16 has a proximal rod engaging portion 76 and a distal bone engaging portion 78. The proximal portion 76 of the depth guide member 16 includes a mounting plate 80 having a substantially hemispherical slot 82 formed therein. The hemispherical slot 82 is defined by end wall 83 and inner sidewalls 84 which extend from end wall 83. The dimensions of the slot 82 should be sufficient to enable the elongate rod member 14 to fit therein. Further, the mounting plate should have a thickness sufficient to enable a portion of the mounting plate 80 that is adjacent to end wall 83 to be engaged with the surface features 60 of the elongate rod member 14. In such an engagement, the mounting plate 80 extends in a direction substantially transverse to the longitudinal axis 100 of the elongate rod member 14.

The distal bone engaging portion 78 of the depth guide member 16 includes at least one prong element 86 that extends distally from the mounting plate 80. In an exemplary embodiment, the distal bone engaging portion 78 includes a pair of opposed, parallel, prong elements 86A and 86B that extend distally from the mounting plate 80. Each prong element 86 has a first portion 87 that is substantially coaxial with longitudinal axis 100, and a second, distal portion 88 that is angled with respect to the first portion 87.

The prong elements 86 of the depth guide member 16 may be constructed at various angles and with various curvatures. In an exemplary embodiment, the second portion 88 of the prong element 86 forms an angle (α), in the range of about 130 to 140 degrees, relative to the first portion 87 of the prong element. Preferably, the prong elements should also be spaced apart by a sufficient distance to provide clearance over an outer surface 96 of femoral stem 90 as illustrated in FIGS. 6 and 7. In an exemplary embodiment, the prong elements may be spaced apart by a distance 89 in the range of about 1.5 to 3.0 centimeters.

In an exemplary embodiment, the second, distal portion 88 of prong elements 86 tapers to a substantially rounded end portion 91. Those of ordinary skill in the art will readily recognize that other suitable shapes for the end portion 91 may also be used. The second, distal portion 88 may further include at least one stem centralizing protrusion or tab, not shown, disposed thereon effective to center the prosthetic stem within the bone cavity. Such centralizing tabs may be disposed on an inner surface of the prong elements and would extend distally beyond the distal end of the prong elements. Additionally, the thickness of the centralizing tabs would be approximately equal to the thickness of the desired cement mantle which would surround the femoral stem after implantation.

Figure 5:
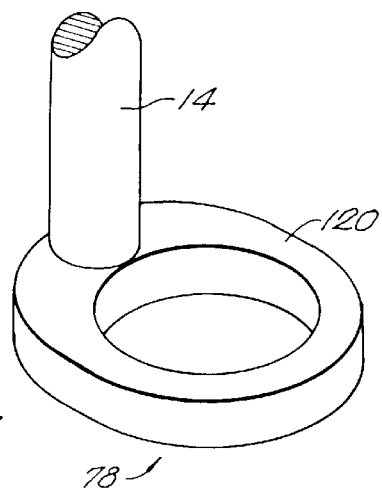
FIG. 5 is a perspective view of a bone engaging portion of an alternative depth guide member.

As shown in FIG. 5, another embodiment of the bone engaging portion 78 may be in the form of a partial or complete loop 120. In an embodiment in which the bone engaging portion 78 is in the form of complete loop, the loop may be circular. Such a circular loop 120 preferably has an inner diameter large enough to slide over the outer surface 96 of the femoral stem 90. The distal bone engaging portion 78 of the depth guide member 16 may also take on other configurations which may be selected by a person of ordinary skill in the art for the intended use of the stem inserter device 10.

Adjustment of the depth guide member 16 is important to accurately and easily position the depth guide member 16 on the stem inserter device 10 for proper insertion of the femoral stem. Various engagement mechanisms can be utilized to selectively control the position of the depth guide member 16 with respect to the elongate rod member 14. In one embodiment, illustrated in FIGS. 1, 2, 6 and 7, a "tongue and groove" type of system is utilized to control such vertical adjustment. The depth guide member 16 has a mounting plate 80 which is adapted to engage with at least one pair of parallel grooves 60 on the elongate rod member 14. To effect such an engagement, the depth guide member 16 is aligned from a bottom side 49 of the rod member 14, with one pair of opposed grooves 60 on the elongate rod member 14. Alignment is accomplished by positioning the hemispherical opening 82 of mounting plate 80 proximate the desired pair of opposed grooves 60 as shown in FIGS. 1 and 3. The depth guide member 16 is then slidably positioned into engagement with the grooves such that a positive engagement is achieved.

The depth guide member 16 is properly engaged when end wall 83 of mounting plate 80 abuts the bottom side 49 of elongate rod member 14. In such an engagement, the mounting plate 80 of depth guide member 16 is oriented in a direction substantially transverse to the longitudinal axis 100 of the elongate rod member 14 and the second, distal portion 88 of each prong element 86 protrudes beyond the distal end 42 of the elongate rod member 14.

The surgical device and system of the present invention may be employed in a variety of surgical applications, particularly those related to hip prostheses, and more particularly to the insertion of a femoral component of a hip prosthesis. Referring to FIGS. 6 and 7, the stem inserter device 10 is shown engaged with the femoral stem implant 90. In an exemplary embodiment, as the depth guide member 16 is moved from its range of possible positions, i.e. distal-most position to the proximal-most position, the two prong elements 86A, 86B are positioned into close proximity with, and alternatively, may even directly contact the outer surface 96 of the femoral stem 90. The second portions 88 of prong elements 86 are then aligned with a corresponding resection level marking or indicia 98 placed on the femoral stem 90. When the femoral stem 90 is inserted into the prepared femoral bone cavity, the distal portions 88 of the prong elements 86 will come into contact with a plane of calcar bone corresponding to the particular resection level marking to indicate the proper insertion depth for the femoral stem.

The surgical device as described herein may be made from a variety of biocompatible materials, including stainless steel, titanium, anodized aluminum or other similar metals and metal alloys.

One of ordinary skill will appreciate that various modifications may be made to the invention described and claimed herein without exceeding the scope of the invention. For example, a pawl and detent type of mechanism or set screw mechanism can be incorporated to facilitate vertical adjustment of the depth guide member with respect to the elongate rod member.

What is claimed is:

1. A prosthetic stem inserter device comprising:
   an elongate rod member having a proximal handle portion and a distal portion, the distal portion having a plurality of surface features formed thereon which define a series of predetermined stem insertion depths; and
   a depth guide member having a proximal portion removably and replaceably engageable with the surface features on the elongate rod member and a distal, bone engaging portion that protrudes beyond a distal end of the elongate rod member.

2. The device of claim 1, further comprising:
   a distally protruding member formed on the distal end of the elongate rod member, the protruding member having a size and shape effective to engage a notch formed in a prosthesis.

3. The device of claim 1, wherein the surface features comprise grooves formed on the elongate rod member.

4. The device of claim 3, wherein the grooves are parallel to each other and extend in a direction generally transverse to a longitudinal axis of the elongate rod member.

5. The device of claim 4, wherein the plurality of parallel grooves are uniformly spaced apart in the longitudinal direction by a distance in the range of about 2 to 8 mm.

6. The device of claim 5, wherein the grooves have a depth in the range of about 2 to 4 mm.

7. The device of claim 1, wherein the proximal portion of the depth guide member comprises a mounting plate having a substantially hemispherical slot formed therein, the mounting plate having a thickness, at the hemispherical slot, sufficient to enable the plate member to be engaged with the surface features of the elongate rod member such that the plate extends in a direction substantially transverse to the longitudinal axis of the elongate rod member.

8. The device of claim 7, wherein the distal bone engaging portion of the depth guide member comprises at least one prong element that extends distally from the plate.

9. The device of claim 7, wherein the distal bone engaging portion of the depth, guide member comprises a pair of opposed, parallel, prong elements that extend distally from the plate.

10. The device of claim 9, wherein each prong of the pair of prong elements has a first, longitudinally extending portion and a second portion that is angled with respect to the first portion.

11. The device of claim 10, wherein the second portion of the prong element is angled in the range of about 130 to 140 degrees relative to the first portion of the prong element.

12. The device of claim 11, wherein the pair of prong elements are spaced apart by a distance in the range of about 1.5 to 3.0 centimeters.

13. A prosthetic stem inserter device for inserting a prosthetic stem at a desired depth within a femur comprising:
   an elongate rod member having a proximal handle portion and a distal portion, the distal portion having a surface feature effective to selectively engage a prosthesis element and at least one indicia formed thereon, which defines a stem insertion depth; and
   a bone-engaging depth guide member having a proximal portion movably mounted upon the elongate rod member and a distal portion that protrudes beyond a distal end of the elongate rod member to engage the femur at the desired depth of insertion.

* * * * *